US009688626B2

(12) United States Patent
Wang et al.

(10) Patent No.: US 9,688,626 B2
(45) Date of Patent: Jun. 27, 2017

(54) UPGRADING PARAFFINS TO DISTILLATES AND LUBRICANT BASESTOCKS

(71) Applicants: Kun Wang, Bridgewater, NJ (US); Suzzy Chen Hsi Ho, Princeton, NJ (US); William N. Olmstead, Basking Ridge, NJ (US)

(72) Inventors: Kun Wang, Bridgewater, NJ (US); Suzzy Chen Hsi Ho, Princeton, NJ (US); William N. Olmstead, Basking Ridge, NJ (US)

(73) Assignee: ExxonMobil Research and Engineering Company, Annadale, NJ (US)

( * ) Notice: Subject to any disclaimer, the term of this patent is extended or adjusted under 35 U.S.C. 154(b) by 0 days.

(21) Appl. No.: 14/956,477

(22) Filed: Dec. 2, 2015

(65) Prior Publication Data
US 2016/0168048 A1 Jun. 16, 2016

Related U.S. Application Data

(60) Provisional application No. 62/092,485, filed on Dec. 16, 2014.

(51) Int. Cl.
C07C 2/76 (2006.01)
C07C 2/82 (2006.01)
(Continued)

(52) U.S. Cl.
CPC .............. *C07C 407/00* (2013.01); *C07C 1/24* (2013.01); *C10G 50/02* (2013.01); *C10G 69/126* (2013.01);
(Continued)

(58) Field of Classification Search
CPC .. C07C 2/76; C07C 2/82; C07C 29/00; C10G 53/14
(Continued)

(56) References Cited

U.S. PATENT DOCUMENTS 2,845,461 A  7/1958  Winkler et al.
3,478,108 A  11/1969 Grane
(Continued)

FOREIGN PATENT DOCUMENTS

CA  1103913 A   6/1981
DE  2453863 A1  5/1975
(Continued)

OTHER PUBLICATIONS

PCT/US2015/063394 International Search Report and Written Opinion dated Mar. 18, 2016.
(Continued)

Primary Examiner — Thuan D Dang
(74) Attorney, Agent, or Firm — Andrew T. Ward

(57) ABSTRACT

A process for converting light paraffins (especially $C_3$-$C_5$) to middle distillate and higher boiling range liquid hydrocarbons by (1) oxygen or air oxidation of iso-paraffins to alkyl hydroperoxides; (2) conversion of alkyl hydroperoxides to dialkyl peroxides; (3) radical coupling of paraffins using the dialkyl peroxides as radical initiators forming heavier hydrocarbon products; and (4) fractionation of the heavy hydrocarbon products. The net reaction is catalytically converting light paraffins to heavier hydrocarbons using oxygen or air to effect the conversion.

28 Claims, 3 Drawing Sheets

(51) Int. Cl.

| | |
|---|---|
| *C07C 29/00* | (2006.01) |
| *C10G 53/14* | (2006.01) |
| *C07C 407/00* | (2006.01) |
| *C10L 1/04* | (2006.01) |
| *C10G 50/02* | (2006.01) |
| *C10G 69/12* | (2006.01) |
| *C07C 1/24* | (2006.01) |

(52) U.S. Cl.
CPC ........ *C10L 1/04* (2013.01); *C10G 2300/1025* (2013.01); *C10G 2300/1081* (2013.01); *C10G 2400/02* (2013.01); *C10G 2400/04* (2013.01); *C10G 2400/08* (2013.01); *C10L 2290/543* (2013.01); *Y02P 20/127* (2015.11)

(58) Field of Classification Search
USPC ......... 585/310, 700, 709; 208/49; 568/909.8
See application file for complete search history.

(56) References Cited

U.S. PATENT DOCUMENTS

| | | |
|---|---|---|
| 3,594,320 A | 7/1971 | Orkin |
| 3,775,325 A | 11/1973 | Kerfoot et al. |
| 3,862,024 A | 1/1975 | Favis |
| 4,140,619 A | 2/1979 | van der Wiel et al. |
| 4,175,278 A | 11/1979 | Sato et al. |
| 4,408,081 A | 10/1983 | Foster |
| 4,594,172 A | 6/1986 | Sie |
| 4,618,737 A | 10/1986 | Chester et al. |
| 4,883,581 A | 11/1989 | Dickakian |
| 4,911,821 A | 3/1990 | Katzer et al. |
| 4,913,794 A | 4/1990 | Le et al. |
| 4,919,788 A | 4/1990 | Chen et al. |
| 4,975,177 A | 12/1990 | Garwood et al. |
| 4,990,713 A * | 2/1991 | Le .................... C10G 50/02 585/332 |
| 4,997,543 A | 3/1991 | Harandi et al. |
| 5,008,460 A | 4/1991 | Garwood et al. |
| 5,021,142 A | 6/1991 | Bortz et al. |
| 5,037,528 A | 8/1991 | Garwood et al. |
| 5,149,885 A | 9/1992 | Jubin, Jr. |
| 5,162,593 A | 11/1992 | Maffia et al. |
| 5,171,916 A | 12/1992 | Le et al. |
| 5,243,084 A | 9/1993 | Cochran et al. |
| 5,271,825 A | 12/1993 | Bortz et al. |
| 5,288,919 A | 2/1994 | Faraj |
| 5,306,416 A | 4/1994 | Le et al. |
| 5,345,009 A | 9/1994 | Sanderson et al. |
| 5,705,724 A | 1/1998 | Collins et al. |
| 5,750,480 A | 5/1998 | Xiong et al. |
| 7,034,189 B1 | 4/2006 | Kollar |
| 7,723,556 B2 | 5/2010 | Elomari et al. |
| 7,732,654 B2 | 6/2010 | Elomari et al. |
| 7,973,204 B2 | 7/2011 | Elomari et al. |
| 2008/0253936 A1 | 10/2008 | Abhari |
| 2016/0168048 A1 | 6/2016 | Wang et al. |

FOREIGN PATENT DOCUMENTS

| | | |
|---|---|---|
| DE | 298521 A5 | 2/1992 |
| EP | 0104729 A2 | 4/1984 |
| EP | 0567336 B2 | 12/1995 |
| FR | 2210656 A1 | 7/1974 |
| FR | 2210657 A1 | 7/1974 |
| JP | 49034903 A | 3/1974 |
| JP | 51012802 A | 1/1976 |
| JP | 60108495 A | 6/1985 |
| NL | 7510598 A | 3/1977 |
| PL | 63556 Y1 | 12/1969 |
| SU | 1068467 A1 | 1/1984 |
| SU | 438293 A1 | 11/1984 |
| SU | 1525196 A1 | 11/1989 |
| SU | 1778148 A1 | 11/1992 |
| SU | 1799902 A1 | 3/1993 |
| SU | 1810378 A1 | 4/1993 |

OTHER PUBLICATIONS

Wallner et al., "Analytical Assessment of C2-C8 Alcohols as Spark-Ignition Engine Fuels", Proceddings of the FISITA 2012 World Automotive Congress, Nov. 7, 2012, pp. 15-26, vol. 3, Springer.

Unknown, "Advanced Motor Fuels", Implementing Agreement for Advanced Motor Fuels, hftp://www.iea-amf.org/content/fuel_information/butanol/properties. Feb. 2, 2017.

Ghosh et al., "Development of a Detailed Gasoline Composition-Based Octane Model", Industrial & Engineering Chemistry Research, Nov. 24, 2005, pp. 337-345, vol, 45, iss, 1, ACS Publications.

Perdih et al., "Topological Indices Derived from Parts of a Universal Matrix", Acta Chimica Slovenica, Apr. 28, 2006, pp. 180-190, vol. 53, Slovenian Chemical Society.

Sust, "Studies on the synthesis of lubricating oils using olefins from technical C5-fractions", Energy Res., 1983, vol. 8, iss. 1, abstract only.

Grudzien, "Selective solvent separation of shale oil fractions to obtain raw material for polymerization", Koks, Smola, Gaz, 1971, pp. 336-339, vol. 16, iss. 12, abstract only.

Ouyang et al., "Production technique of synthetic hydrocarbon lube oil with coking top cycle oil", Runhuayou, 2001, pp. 17-20, vol. 15, iss. 5, abstract only.

Kuliev et al,, "Production of lubricating oils by alkylation of an aromatic raw material", Sbornik Trudov—Akademiya Nauk Azerbaidzhanskoi SSR, Institut Neftekhirnicheskikh Protsessov im. Yu. G. Mamedalieva, 1973, pp. 128-128, vol. 5, abstract only.

Kuliev et al., "Manufacture of synthetic lubricating oils by alkylation of a secondary oil refining product", Chemische Technik, 1971, vol. 23, iss. 1, abstract only.

Takahashi et al., "Designed Oil Products from Cracked Bottom Oil", Bull Jap Petrol Inst, May 1971, pp. 103-108, vol, 13, iss. 1, abstract only.

Mursalova et al., "Alkylation of Benzene with a Wide Fraction of Alpha-Olefins (30 Degrees-250 Degrees C) Obtained by Cracking N-Paraffins (Separated in the Urea Dewaxing) of a Transformer Oil", Dokl Abad Nauk Azerb SSR, 1969, pp. 20-23, vol. 25, iss, 7, abstract only.

Kuliev, "Alkyl derivatives of petroleum hydrocarbons as lubricating oil basestocks", Khimiya i Tekhnologiya Topliv i Masel, 1997, pp. 34-35, vol. 6, abstract only.

Graves, "STRATCO Effluent Refrigerated H2SO4 Alkylation Process", Chapter 1.2 in Handbook of Petroleum Refining Processes, 3rd Ed., 2004. McGraw-Hill.

Roeseler, "UOP Alkylene Process for Motor Fuel", Chapter 1.3 in Handbook of Petroleum Refining Processes, 3rd Ed., 2004. McGraw-Hill.

Detrick et al., "UOP HF Alkylation Technology", Chapter 1.2 in Handbook of Petroleum Refining Processes, 3rd Ed., 2004. McGraw-Hill.

* cited by examiner

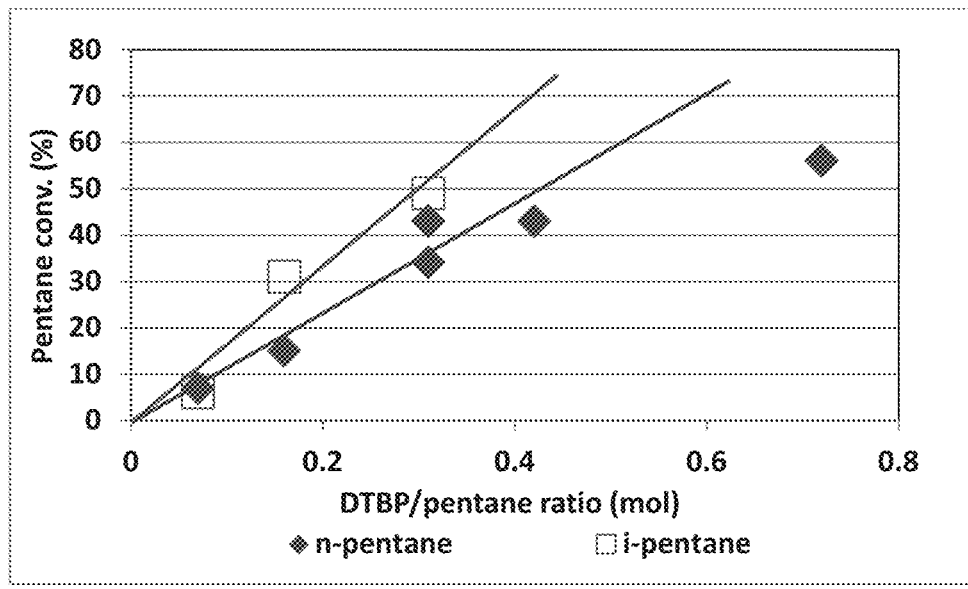
Figure 2. Conversion of pentane vs. the amount of di-t-butyl peroxide used.
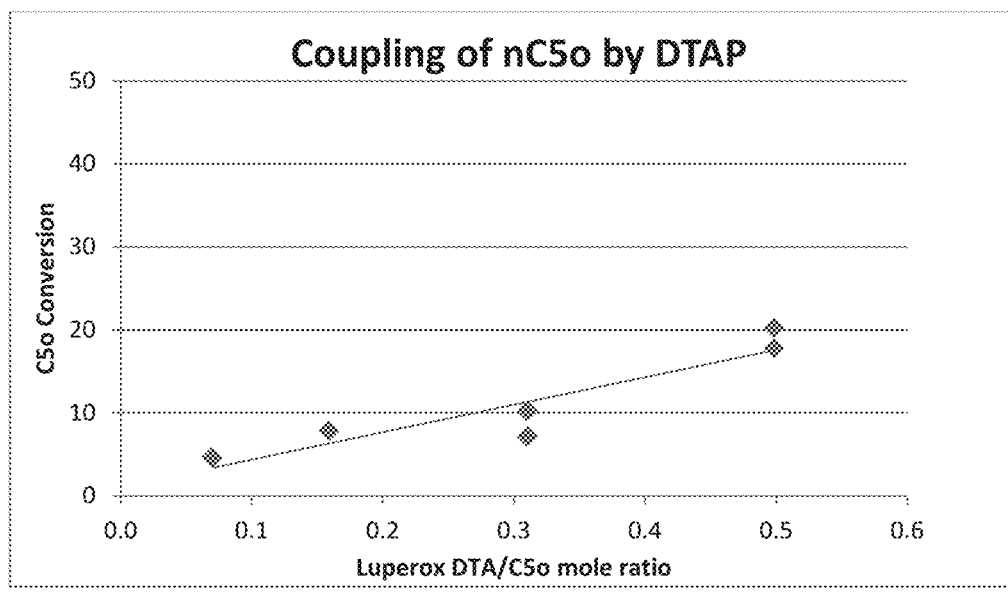
Figure 3. Conversion of n-pentane vs. the amount of di-t-amyl peroxide used.

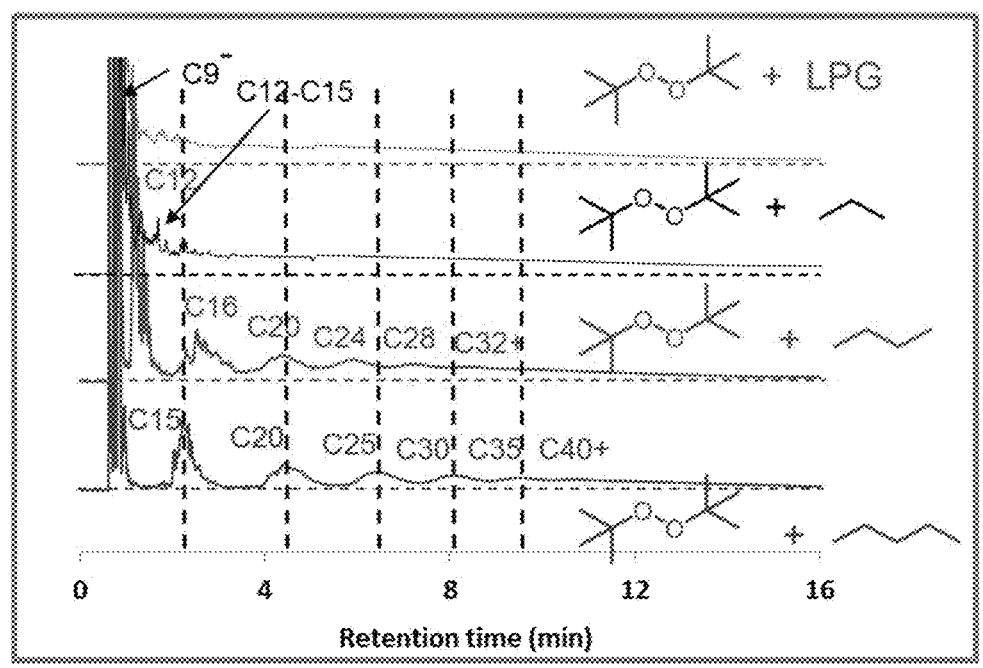
Figure 4. GC of the paraffin coupling products using di-t-butyl peroxide (bottom to top): n-pentane, n-butane, propane, and LPG (1/1 propane/n-butane).

UPGRADING PARAFFINS TO DISTILLATES AND LUBRICANT BASESTOCKS

CROSS-REFERENCE TO RELATED APPLICATIONS

This application claims priority to U.S. Provisional Application Ser. No. 62/092,485 filed Dec. 16, 2014, herein incorporated by reference in its entirety.

FIELD OF THE INVENTION

This invention relates to a process to upgrade paraffins to higher value products such as lubricant basestocks, jet and diesel fuels. The process is particularly applicable to the upgrading of light paraffins ($C_2$-$C_{12}$). Light paraffins of this kind are commonly found in Natural Gas Liquids (NGL), tight oils (light crude oil contained in petroleum-bearing formations of low permeability, often shale or tight sandstone, also referred to as light tight oils), as well as fractions from various refining and/or chemical streams.

BACKGROUND OF THE INVENTION

With the increasing production of shale gas and tight oils, the supply of light paraffins (e.g., $C_2$-$C_8$, especially $C_2$-$C_5$ paraffins) is increasing at an unprecedented rate in the North America region; a large fraction (up to 30%) of NGL, for example, is $C_4$/$C_5$ paraffins. At the same time, demand for $C_4$/$C_5$ molecules is decreasing due to a number of factors: 1) steam crackers switching feed from light naphtha to ethane; 2) shrinkage of gasoline pool in the North American market; and 3) a potential mandate for gasoline Reid Vapor Pressure (RVP) reduction. Although diluent use of $C_5$s for heavy crude is predicted to grow somewhat, the supply of $C_4$s/$C_5$s is quickly outpacing demand and the imbalance will become worse with time. Profitable dispositions for ethane (e.g., cracking to make ethylene) and propane (e.g., dehydrogenation making propylene) exist. Upgrading $C_4$/$C_5$ paraffins to higher value and large volume products, while desirable, remains challenging. Conversion of $C_4$/$C_5$ paraffins to heavier hydrocarbon products such as kerojet, diesel fuels as well as lubricant basestocks would provide a large volume and higher value outlet to help alleviate the excess of light ends in the North American market; but there is no current commercial process directly converting light paraffins to heavier hydrocarbons such as these. Conventional upgrading practices first convert light paraffins to olefins via cracking or dehydrogenation, followed by olefin chemistries such as oligomerization or polymerization, alkylation, etc. to build higher molecular weight molecules. A number of technologies are known to convert light paraffins to aromatics such as BTX (benzene, toluene, and xylenes). Examples of such technologies include the Cyclar™ process developed by UOP and the M2-Foming developed by Mobil Oil Corporation.

SUMMARY OF THE INVENTION

We have now developed a process for converting paraffins to higher boiling range liquid hydrocarbons including gasoline, middle distillates (kerojet, heating oil, road diesel fuel), and, at the higher range of molecular weight and boiling point, lubricant basestocks. The process is especially applicable to paraffins in the $C_2$-$C_{12}$ range, and particularly light paraffins ($C_3$-$C_5$) which are currently in good supply.

The process according to the invention comprises four major steps: (1) oxygen (air) oxidation of iso-paraffins to alkyl hydroperoxides; (2) conversion of alkyl hydroperoxides to dialkyl peroxides; (3) radical coupling of paraffins using the dialkyl peroxides as radical initiators to form heavier hydrocarbon products; (4) fractionation of the heavy hydrocarbon products, and optionally, (5) hydro-finishing of the heavy hydrocarbon products. The net reaction is catalytically converting light paraffins to higher value products using oxygen (air) to effect the conversion.

The net reaction is oxygen (air) and paraffins giving gasoline, jet, and diesel fuels, as well as water and an alcohol. By controlling the reaction severity for radical coupling in Step 3 above, higher molecular weight materials such as lubricant basestocks can be obtained. Depending on the nature of the iso-paraffin, the resulting alcohol by-product (e.g., 2-methyl-2-butanol from iso-pentane, tert-butyl alcohol from isobutane) can be blended directly with gasoline, converted to an olefin as a chemical product via dehydration (e.g., iso-butylene from tert-butyl alcohol), or etherified with an alcohol such as methanol or ethanol making ether as gasoline blend, e.g., MTBE (methyl-tert-butyl ether), ETBE (ethyl-tert-butyl ether), MTAE (methyl-tert-amyl ether), and ETAE (ethyl-tert-amyl ether). Alternatively, the iso-olefins can be converted further into gasoline, jet, diesel, or basestocks via oligomerization or alkylation.

DRAWINGS

FIG. 2 shows the conversion of pentane (n- or i-) vs. the amount of di-t-butyl peroxide used (DTBP/pentane molar ratio) for the coupling.

FIG. 3 shows the conversion of n-pentane vs. the amount of di-t-amyl peroxide used (DTA/pentane molar ratio) for the coupling.

FIG. 4 shows the gas chromatographs for the coupling products from n-pentane, n-butane, propane, and LPG using di-t-butyl peroxide.

DETAILED DESCRIPTION

Figure 1:
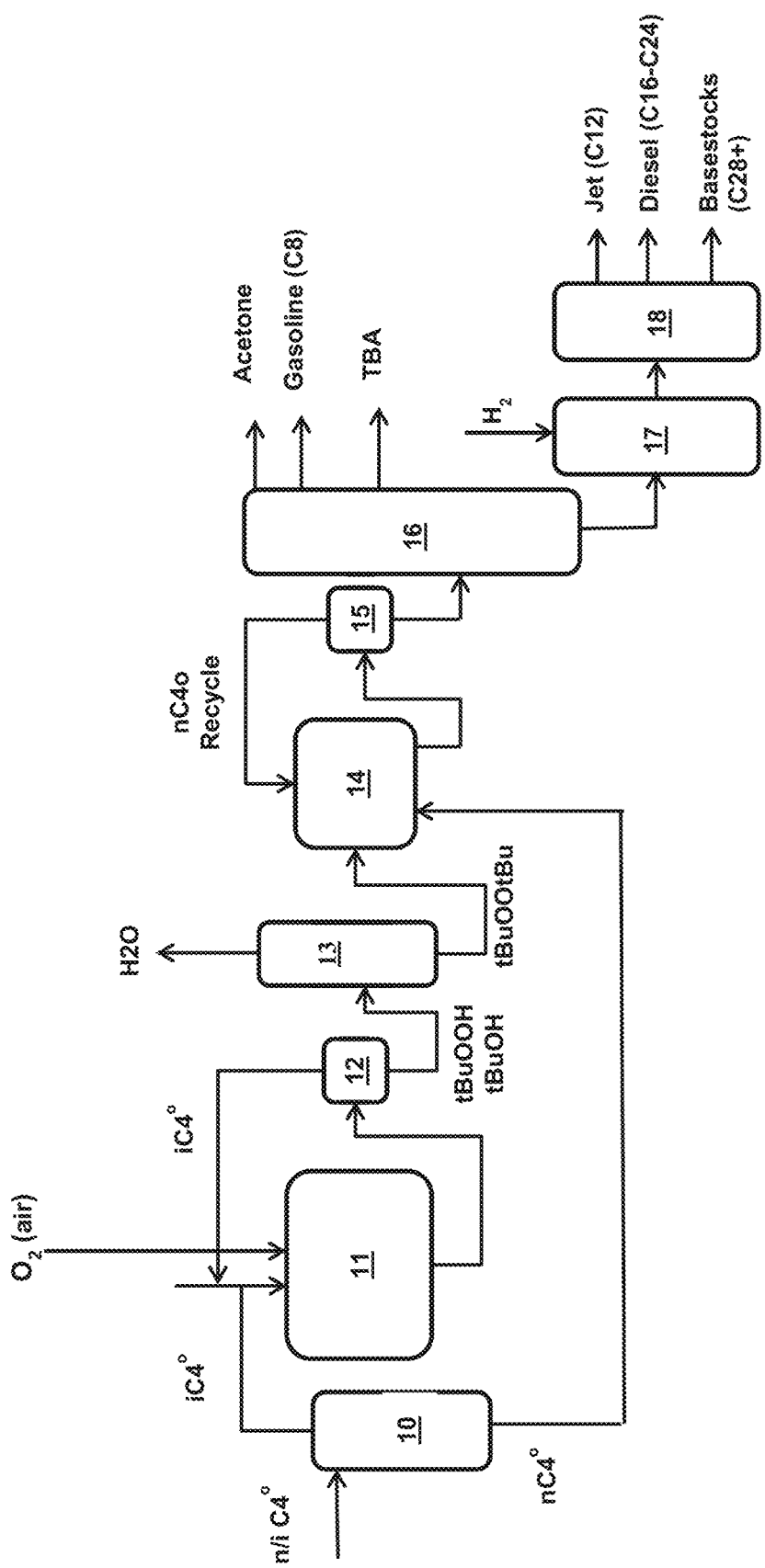
FIG. 1 shows a process flow scheme for converting butanes to higher value products.

The present process may be used with a wide range of paraffins, extending from $C_2$ to $C_{12}$, but is particularly applicable to use with propane, butanes, and pentanes; the latter two are under regulatory pressure limiting its blending in the gasoline pool for compliance with RVP regulations. Other paraffins of higher molecular weight may be present but since they may be more valuable for other uses, efforts will normally be made to obtain a clean cut point permitting the $C_6$s and higher to be separated from the $C_3$, $C_4$s, and $C_5$s. For brevity, the invention will be described below in connection with the upgrading of butanes and pentanes, although it has the broader utility mentioned above as well as shown in the examples.

The process flow scheme in the Figure illustrates the operation of the process in the context of a petroleum refinery using butanes as the light paraffin feed. A mixture of normal- and iso-butane comprising iso-butane in the weight range of 5-90%, for example in the range 10-80% and more usually 20-70%, is introduced into a fractionator 10 similar in function to the iso-stripper of an isoparaffin/olefin process unit in which the iso-butane (bp −12° C.) is separated from the n-butane (bp −1° C.). Iso-pentane (bp 27.7° C.) can also be readily separated from n-pentane (bp 36.1° C.) by fractionation. The iso-butane passes to the oxidation reactor in which the iso-butane is oxidized with $O_2$ or air to form t-butyl hydroperoxide and, depending on the conversion level, varying concentrations of t-butyl alcohol. Iso-butane oxidation is a well-established commercial process for making tert-butyl hydroperoxide (TBHP) for propylene oxide manufacture; variants of the process are described, for example, in U.S. Pat. Nos. 2,845,461; 3,478,108; 4,408,081 and 5,149,885. EP 0567336 and U.S. Pat. No. 5,162,593 disclose co-production of TBHP and tertiary-butyl alcohol (TBA); TBA is another reactant used in the present process scheme to convert tert-butyl hydroperoxide to di-tert-butyl peroxide (as in Step 2 above) and accordingly, the iso-butane oxidation process is a practical source of these two reactants. Iso-pentane and other iso-paraffins may be oxidized by $O_2$ or air in a similar manner. Typical oxidation conditions are: temperature in the range of 110-150° C. (preferably 130 to 140° C., e.g., about 135° C.), at a pressure of 2000-5500 kPag (about 300-800 psig) and preferably about 2000-3500 kPag (about 300-510 psig) with a residence time of 2-24 h (preferably 6-12 h) to give a targeted conversion of 15%-50%, preferably 25-48%. Selectivity to TBHP of 50-80% and to TBA of 20-50% is typical. Either air or oxygen ($O_2$) can be used for the oxidation, as long as the $O_2$ to hydrocarbon vapor ratio is kept outside the explosive regime. The oxidizer effluent is taken to flash drum 12 in which unreacted iso-butane is separated and recycled to the oxidation reactor. The pressure for the oxidation reactor should be sufficient to maintain the iso-paraffin in the liquid phase although this becomes more difficult as the molecular weight of the iso-paraffins decreases.

The n-butane separated in the fractionator 10 may be isomerized to form iso-butane in a butane isomerization unit (e.g., UOP's Butamer™ technology) such as widely used in conjunction with olefin/isoparaffin alkylation units and the isomerized product returned to the fractionator. Processes for pentane, hexane and light naphtha isomerization such as the UOP Par-Isom™ or Penex™ processes are also available and widely used in the refining industry and may be adapted for use in the present process according to the paraffin supply.

tert-Butyl hydroperoxide (TBHP) and tert-butyl alcohol from the oxidation step are sent to reactor 13, where makeup t-butyl alcohol (TBA) is added when necessary. An acid catalyst such as Amberlyst™ resin, Nafion™ resin, aluminosilicates, acidic clay, zeolites (natural or synthetic), silicoaluminophosphates (SAPO), heteropolyacids, acidic oxides such as tungsten oxide on zirconia, molybdenum oxide on zirconia, sulfuated zirconia, liquid acids such sulfuric acid, or acidic ionic liquids is used to promote the conversion of TBHP and TBA into di-t-butyl peroxide (DTBP) according to the equation:

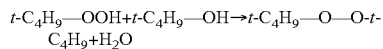

The conversion of the hydroperoxide and alcohol to dialkyl peroxides is also a known process. For example, U.S. Pat. No. 5,288,919 describes the use of an inorganic heteropoly and/or isopoly acid catalyst for the reaction of tertiary butyl alcohol with tertiary butyl hydroperoxide. The conjoint production of di-tert-butyl peroxide and tert-butyl alcohol from tert-butyl hydroperoxide is also described in U.S. Pat. No. 5,345,009. A preferred configuration for this reactor uses reactive distillation where product water is continuously removed as overhead by-product.

DTBP is sent to the next reactor in sequence, 14, to initiate free radical coupling of n-butane fed from fractionator 10. Typical reaction conditions for the coupling reaction include a temperature of 100-170° C., preferably about 150° C. with a pressure maintained high enough to ensure that the paraffins stay in the liquid phase, suitably at 3,500-10,000 kPag (about 500-1500 psig), preferably about 8000 kPag (about 1160 psig). Residence time is normally in the range of 2-10 hr, typically about 4 h. The molar ratio of DTBP to the paraffins to be coupled is in the range of 0.01-100, preferably in the range of 0.05-10, more preferably in the range of 0.1-2. Complete conversion of DTBP is normally achieved in this reactor.

Unreacted n-butane is then separated in flash unit 15 from the coupled paraffin products in the range of $C_8$ and higher. The unreacted n-butane is recycled to coupling reactor 14 while the coupled products are fractionated in column 16 to remove trace water, acetone by-product and TBA. The heavy ends are then optionally hydrofinished in reactor 17 to remove residual unsaturation and/or oxygenates; and finally separated in fractionator 18 into various carbon number range products such as middle distillates including jet and diesel, as well as lubricant basestocks. Typically hydrofinishing conditions are: temperature in the range of 150-350° C., preferably 200-250° C. and $H_2$ pressure of 1,400-7,000 kPag (about 200-1000 psig), preferably 2800-4100 kPag (about 400-600 psig). Conventional hydrogenation catalysts such as supported metal (Pt, Pd, Rh, Ru, Ir, Co, Ni, Fe, Cu, Mo, W, Re, Sn, either a single metal or binary or ternary alloy) on alumina, silica, zirconia, titania, carbon, aluminosilicates, zeolites (natural or synthetic), silicoaluminophosphates (SAPO) can be used for the hydrofinishing step. Preferred catalysts are Pd, Pt, Ru, Rh (either alone or alloy) supported on alumina, silica (either amorphous or mesoporous), or aluminosilicates.

Although a mixture of normal- and iso-butanes is used in the exemplary embodiment above, mixtures of normal-, iso-, neo-, and cyclo-paraffins can be used as feed and effectively coupled using the process of this invention. The feed paraffins in the coupling step 3 may have the same or different carbon numbers as the iso-paraffins of the oxidation and isomerization steps and so are typically in the range of $C_2$ to $C_{12}$. Examples of the paraffin in the feed include, ethane, propane, normal-butane, iso-butane, normal-pentane, iso-pentane, neo-pentane, cyclo-pentane, normal-hexane, 2-methyl-pentane, 3-methyl-pentane, 2,2-dimethyl-butane, 2,3-dimethyl-butane, cyclo-hexane, methyl-cyclo-pentane, either individually or mixtures thereof. The feed may comprise some level of olefins, such as up to 50 wt %, preferably lower than 10 wt %, more preferably lower than 5 wt % olefins. Examples of the olefins include ethylene, propylene, normal or iso-butenes, butadiene, normal (1-pentene, cis- or trans-2-pentene) or iso-pentenes (2-methyl-1-butene, 3-methyl-1-butene, 2-methyl-2-butene), cyclopentene, cyclopentadiene, isoprene, cis- or trans-piperylene, either individually or mixtures thereof. Additionally, natural gas liquids, liquid petroleum gas, and refinery light gas such as light virgin naphtha (LVN) or light catalytic naphtha (LCN), can also be upgraded using the process of this invention.

The TBA from the primary fractionator 16 can be recycled, when needed, either fully or partially to reactor 13 for the formation of dialkyl peroxides. The excess TBA can be converted to ether by reacting with an alcohol such as methanol or ethanol. The etherification can be performed either in a single step or by a two-step process where the TBA is first converted to iso-butylene followed by reaction with the alcohol. The reaction can be carried out in a fixed-bed reactor or a catalytic distillation reactor where an acid catalyst is employed. Examples of the acid catalysts include resins such as Dowex, Amberlyst, Nafion, sulfuric acid, sulfonic acid, phosphoric acid (neat or solid-supported on silica, alumina, or clay), acidic clay, aluminosilicate, zeolite, silicoaluminophosphate, acidic oxides such as tungsten oxide on zirconia, molybdenum oxide on zirconia, sulfuated zirconia, acidic ionic liquids; Lewis acids such as aluminum chloride or boron trifluoride. The reaction is suitably carried out at a temperature of 100-400° C., preferably 150-350° C. and a pressure of 700-3450 kPag (about 100-500 psig), preferably 1,000-2760 kPag (about 150-400 psig).

The TBA recovered from the primary fractionator can be used as a chemical product, fuel blend, or dehydrated giving iso-butylene. Dehydration is typically carried out in the vapor phase at a temperature of 150-450° C., preferably 200-350° C. and a pressure of 700-3450 kPag (about 100-500 psig), preferably 1,000-2,070 kPag (about 150-300 psig) in fixed-bed or slurry reactors. An acidic catalyst is used, such as those described above for the etherification reaction.

The iso-butylene formed after TBA dehydration can be used as a chemical intermediate for the production of polymers, rubber, or hydrocarbon resins. Optionally and if desired, the iso-olefins can be converted to gasoline, kero-jet, diesel, and lubricant range products via oligomerization. The oligomerization can be performed in either slurry or fixed-bed reactors using an acid catalyst such as those described above for the etherification reaction. The reaction is suitably carried out at a temperature of 100-350° C., preferably 150-250° C.; and a pressure of 200-500 psig, preferably 300-400 psig.

The iso-butylene formed after TBA dehydration can be converted to higher molecular weight products such as gasoline, kero-jet, or diesel via alkylation. Alkylation can be carried out using an acid catalyst such as sulfuric acid, hydrofluoric acid, or zeolites in the FAU, MOR, MFI, or MWW families. The isobutylene is fed with an isoparaffin such as iso-butane or iso-pentane with an iso-paraffin/olefin (i/o) ration of 1.2-50, preferably 1.5-20, and more preferably 5-10. The reaction temperature is maintained appropriately depending on the catalyst used: e.g., 0-5° C. for sulfuric acid or HF; 10-200° C. for solid catalysts such as zeolites.

Additional Embodiments

Embodiment 1. A process for the conversion of a feed comprising paraffins to higher molecular weight hydrocarbons which comprises; oxidizing iso-paraffins from the feed with air or oxygen to form alkyl hydroperoxides or isomerizing a fraction of the normal paraffins in the feed to isoparaffins; and separating the isoparaffins and oxidizing the separated isoparaffins with air or oxygen to form alkyl hydroperoxides; converting the alkyl hydroperoxides to dialkyl peroxides; and coupling a feed comprising paraffins using the dialkyl peroxides as radical initiators to form hydrocarbon products of higher molecular weight.

Embodiment 2. A process according to embodiment 1, where the feed paraffins are iso-paraffins, normal-paraffins, neoparaffins, cyclic paraffins, or mixtures thereof with carbon numbers in the range of 2 to 12 with the same or different carbon numbers as the iso-paraffins.

Embodiment 3. A process according to any of the previous embodiments, where the feed paraffins comprise less than 50 wt % olefins; and the carbon numbers of the paraffins are in the range of 2 to 12 with the same or different carbon numbers as the iso-paraffins.

Embodiment 4. A process according to any of the previous embodiments, where the feed paraffins comprise less than 10 wt % olefins; and the carbon numbers of the paraffins are in the range of 2 to 12 with the same or different carbon numbers as the iso-paraffins.

Embodiment 5. A process according to any of the previous embodiments, where the feed paraffins comprise less than 5 wt % olefins; and the carbon numbers of the paraffins are in the range of 2 to 12 with the same or different carbon numbers as the iso-paraffins.

Embodiment 6. A process according to any of the previous embodiments where the feed is light virgin naphtha.

Embodiment 7. A process according to any of the previous embodiments where the feed is liquefied petroleum gas (LPG).

Embodiment 8. A process according to any of the previous embodiments where the feed is a mixture of propane, butanes and/or pentanes.

Embodiment 9. A process according to any of the previous embodiments in which the feed paraffins comprise butanes.

Embodiment 10. A process according to embodiment 9 in which the feed comprises a mixture of n-butane and iso-butane comprising 5 to 90 wt % iso-butane.

Embodiment 11. A process according to embodiment 9 or 10 in which the feed is n-butane which is isomerized to form iso-butane.

Embodiment 12. A process according to any of the previous embodiments in which the feed paraffins comprise pentanes.

Embodiment 13. A process according to embodiment 12 in which the feed comprises a mixture of n-pentane, iso-pentane, cyclo-pentane, or neo-pentane.

Embodiment 14. A process according to embodiment 13 in which the feed is n-pentane.

Embodiment 15. A process according to any of the previous embodiments which includes the step of fractionating the hydrocarbon products to separate the hydrocarbon products of higher molecular weight.

Embodiment 16. A process according to any of the previous embodiments in which the iso-paraffins are separated from the n-paraffins and the separated n-paraffins are coupled with the dialkyl peroxides to form the hydrocarbon products of higher molecular weight.

Embodiment 17. A process according to any of the previous embodiments in which the iso-paraffins are oxidized to a mixture of alkyl hydroperoxides and alkanols.

Embodiment 18. A process according to any of the previous embodiments in which the alkyl hydroperoxides are converted to dialkyl peroxides by reaction of the alkyl hydroperoxides with alkanol.

Embodiment 19. A process according to embodiment 18 in which the alkyl hydroperoxides are converted to dialkyl peroxides by reaction of the alkyl hydroperoxides with $C_4$ or $C_5$ alkanol.

Embodiment 20. A process according to any of the previous embodiments in which the hydrocarbon products of higher molecular weight formed by the coupling of the feed comprising $C_3$, $C_4$ or $C_5$ paraffins with the dialkyl peroxide are fractionated to separate lower $C_4$ or $C_5$ alkanol and the separated alkanol is partially or fully recycled to step 2 for the formation of dialkyl peroxides.

Embodiment 21. A process according to any of the previous embodiments in which the hydrocarbon products of higher molecular weight formed by the coupling of the feed comprising $C_3$, $C_4$ or $C_5$ paraffins with the dialkyl peroxide are fractionated to separate fuel boiling range hydrocarbons from higher boiling range hydrocarbons.

Embodiment 22. A process according to embodiment 21 in which fuel boiling range hydrocarbons from higher boiling range hydrocarbons are hydro-finished to remove trace oxygenates or unsaturation.

Embodiment 23. A process according to embodiment 22 in which the hydrofinishing is performed at a temperature in the range of 150-350° C. and a hydrogen pressure of 1400-7000 KPag (200-1000 psig).

Embodiment 24. A process according to embodiments 22 or 23 in which the hydrofinishing is performed with a catalyst comprising a metal or an alloy on a support.

Embodiment 25. A process according to embodiment 24 in which the metal or alloy comprises Pt, Pd, Rh, Ru, Ir, Co, Ni, Fe, Cu, Mo, W, Re, or Sn.

Embodiment 26. A process according to embodiment 24 in which the support comprises alumina, silica, zirconia, titania, carbon, aluminosilicates, zeolites (natural or synthetic), or silicoaluminophosphates (SAPO).

Embodiment 27. A process according to any of the previous embodiments in which the hydrocarbon products of higher molecular weight formed by the coupling of the feed comprising $C_4$ or $C_5$ paraffins with the dialkyl peroxide are fractionated to separate lower $C_4$ or $C_5$ alkanol and the alkanol is dehydrated to form iso-olefins.

Embodiment 28. A process according to any of the previous embodiments in which the hydrocarbon products of higher molecular weight formed by the coupling of the feed comprising $C_4$ or $C_5$ paraffins with the dialkyl peroxide are fractionated to separate lower $C_4$ or $C_5$ alkanol and the alkanol is converted into ether by reacting with an alcohol such as methanol or ethanol.

Embodiment 29. A process according to embodiment 27 where the iso-olefins are converted by oligomerization to higher molecular weight products gasoline, kero-jet, diesel, or lubricant basestocks.

Embodiment 30. A process according to embodiment 27 where the iso-olefins are converted by alkylation to higher molecular weight products gasoline, kero-jet, or diesel.

Embodiment 31. A process according to any of the previous embodiments in which the oxidation of step 1 is carried out at a temperature of 110-150° C. and a pressure of 2000-5500 kPag.

Embodiment 32. A process according to any of the previous embodiments in which the oxidation of step 1 is carried out at a temperature of 130-140° C. and a pressure of 2000-3500 kPag.

Embodiment 33. A process according to any of the previous embodiments in which the conversion of alkyl hydroperoxides to dialkyl peroxides in step 2 is carried out by reactive distillation.

Embodiment 34. A process according to any of the previous embodiments in which the coupling reaction of step 3 is carried out at a temperature of 100-170° C. at a pressure of 3,500-10,000 kPag.

EXAMPLES

Example 1

Coupling of n-Pentane to Heavier Hydrocarbons Using Di-t-Butyl Peroxide

This example demonstrates the coupling reaction of n-pentane using di-t-butyl peroxide to form a range of heavier hydrocarbon products.

In a 300-cc autoclave the following were loaded: 50.1 g of n-pentane and 50.9 g of di-t-butyl peroxide (Luperox DI™ from Sigma-Aldrich, 98%). The autoclave was sealed, connected to a gas manifold, and pressurized with 4140 kPag (600 psig) $N_2$. The reactor content was heated under stirring (500 rpm) at a rate of 2° C./min to 150° C. and held for 4 hours. The heat was turned off and the autoclave allowed cooling down to room temperature.

A sample was taken and analyzed by GC, indicating complete conversion of di-t-butyl peroxide and 35% conversion of n-pentane. The autoclave was opened and 20 g more of di-t-butyl peroxide was added and the reactor heated again at 150° C. for 4 h. The reaction mixture was sampled for GC analysis at the end, showing complete conversion of di-t-butyl peroxide and 45% conversion of n-pentane. The reactor content was collected at the end of the run, recovering 87% of the materials loaded. The final products were fractionated using first a rotary evaporator and then Kugelrohr distillation, giving the following fractions. The results are given in Table 1 below.

TABLE 1

| Description | Amount (g) | Carbon No. | Cetane Number* | Density (est'd), g/mL | KV100° C., cSt | KV40° C., cSt | DSC Tg, ° C. |
|---|---|---|---|---|---|---|---|
| Original | 126.22 | | 54.9 | | | | |
| Rotovap Top | 100.16 | t-butanol + $C_5$, 4% $C_{10}$ | 63.1 | | | | |
| Rotovap Bottom | 26 | | — | | | | |
| KugelRohr 45° C. Top | 1.68 | 96% $C_{15}$, 4% $C_{20}$ | 23.1 | 0.858 | | | −113.65 |
| KugelRohr 70° C. Top | 2.5 | 67% $C_{15}$, 31% $C_{20}$, 2% $C_{30}$ | 28.6 | 0.888 | | | −106.24 |
| KugelRohr 105° C. Top | 2.32 | 5% $C_{15}$, 73% $C_{20}$, 20% $C_{25}$ | 26.4 | 0.898 | | | −88.22 |
| KugelRohr 140° C. Top | 2.59 | 14% $C_{20}$, 59% $C_{25}$, 27% $C_{30}$ | 28.1 | 0.958 | <5.5 | 27.65 | −72.61 |
| KugelRohr 140° C. Bottom | 16.44 | 5% $C_{25}$, 95% $C_{30}$+ | 29.6 | 0.965 | 61.03 | | −30.96 |

*Calculated from $^1$H NMR spectra obtained using a Bruker 400 MHz Advance III Spectrometer. Samples were dissolved in chloroform-d ($CDCl_3$) in a 5 mm NMR tube prior to being inserted into the spectrometer magnet. The data was collected at room temperature using a maximum pulse width of 45 degree, 8 seconds between pulses and signal averaging 120 transients. Spectra were referenced by setting the chemical shift of the $CDCl_3$ solvent signal to 7.24 ppm.

Clearly, gasoline, jet, diesel range products were obtained by the n-pentane coupling. In addition, a large percentage of the products falls into the $C_{30}^+$ region, which would provide lubricant basestocks or blend stocks. All product fractions have good low temperature properties as shown by their low glass transition temperatures (Tg). No wax formation was observed using Differential Scanning Calorimetry (DSC). Estimated densities of the fuel products are higher than conventional fuels. Cetane numbers for the fuel fractions are low, consistent with the highly branched nature of the products. $^1$H NMR revealed low concentrations of olefinic hydrogen (<0.5% of total hydrogen) in all fractions of the products; Mass Spectrometry revealed the presence of oxygenates with ketonic functionality in the $C_{30}$+ fraction; the content of Carbon atoms associated with oxygen is estimated to be <3% using quantitative $^{13}$C NMR.

Example 2

Coupling of n-Pentane to Heavier Hydrocarbons Using Varying Amounts of Di-t-Butyl Peroxide In a 300-cc autoclave n-pentane and di-t-butyl peroxide (Luperox DI™ from Sigma-Aldrich, 98%) were loaded according to the desired ratio. The autoclave was sealed, connected to a gas manifold, and pressurized with 4140 kPag (600 psig) $N_2$. The reactor content was heated under stirring (500 rpm) at a rate of 2° C./min to 150° C. and held for 4 hours. The heat was turned off and the autoclave allowed cooling down to room temperature. A sample was taken and analyzed by GC, indicating complete conversion of di-t-butyl peroxide. The conversion of n-pentane vs the amount of di-t-butyl peroxide used is shown in FIG. 2.

Example 3

Coupling of I-Pentane to Heavier Hydrocarbons Using Varying Amounts of Di-t-Butyl Peroxide In a 300-cc autoclave i-pentane and di-t-butyl peroxide (Luperox DI™ from Sigma-Aldrich, 98%) were loaded according to the desired ratio. The autoclave was sealed, connected to a gas manifold, and pressurized with 4140 kPag (600 psig) $N_2$. The reactor content was heated under stirring (500 rpm) at a rate of 2° C./min to 150° C. and held for 4 hours. The heat was turned off and the autoclave allowed cooling down to room temperature. A sample was taken and analyzed by GC, indicating complete conversion of di-t-butyl peroxide. The conversion of i-pentane vs the amount of di-t-butyl peroxide used is shown in FIG. 2.

Example 4

Coupling of n-Pentane to Heavier Hydrocarbons Using Di-t-Amyl Peroxide

In a 300-cc autoclave n-pentane and di-t-amyl peroxide (Luperox DTA™ from Arkema, Inc.) were loaded according to the desired ratio. The autoclave was sealed, connected to a gas manifold, and pressurized with 4140 kPag (600 psig) $N_2$.

The reactor content was heated under stirring (500 rpm) at a rate of 2° C./min to 150° C. and held for 4 hours. The heat was turned off and the autoclave allowed cooling down to room temperature. A sample was taken and analyzed by GC, indicating complete conversion of di-t-amyl peroxide. The conversion of n-pentane vs the amount of di-t-amyl peroxide used is shown in FIG. 3.

Example 5

Atmospheric Distillation of Products from n-Pentane Coupling Using Di-t-Butyl Peroxide Toward a three-necked round-bottom flask was added the n-pentane coupling products from Example 2. Under an atmosphere of $N_2$, the products were distilled to these fractions: 1) n-pentane (cut point: 35° C.); 2) acetone (56° C.); t-butyl alcohol (83° C.). The final temperature was 120° C. and residue remained in the flask was $C_{10}^+$ bottom.

Example 6

Hydrofinishing of the $C_{10}^+$ Bottom from n-Pentane Coupling

An amount of 100 g of the $C_{10}^+$ bottom from Example 5 was loaded into a 300-cc autoclave. The hydrofinishing catalyst contains 0.6 wt % of Pt and 0.6 wt % of Pd supported on silica. An amount of 10 g of the hydrofinishing catalyst was crushed into powder and added to the autoclave. At a hydrogen pressure of 600 psig and a temperature of 250° C., the trace oxygenates were fully converted after 24 hr (as indicated by disappearance of the 1714 $cm^{-1}$ band in IR). The hydrofinished product was also analyzed by $^1H$ NMR and $^{13}C$ NMR; confirming the complete removal of olefinic and oxygenate functionalities.

Example 7

Coupling of n-Butane to Heavier Hydrocarbons Using Di-t-Butyl Peroxide

In a 300-cc autoclave an amount of 56 g of di-t-butyl peroxide was added. Under a $N_2$ pressure, 100 mL of liquid n-butane was charged to the autoclave. The autoclave was then heated to 150° C. for 4 h at a stirring rate of 800 rpm. The heat was turned off and the autoclave allowed cooling down to room temperature. A sample was taken and analyzed by GC, indicating complete conversion of di-t-butyl peroxide. A typical GC trace for the n-butane coupling products is shown in FIG. 4.

Example 8

Coupling of Propane to Heavier Hydrocarbons Using Di-t-Butyl Peroxide

In a 300-cc autoclave an amount of 56 g of di-t-butyl peroxide was added. Under a $N_2$ pressure, 100 mL of liquid propane was charged. The autoclave was then heated to 150° C. for 4 h at a stirring rate of 800 rpm. The heat was turned off and the autoclave allowed cooling down to room temperature. A sample was taken and analyzed by GC, indicating complete conversion of di-t-butyl peroxide. A typical GC trace for the propane coupling products is shown in FIG. 4.

Example 9

Coupling of LPG to Heavier Hydrocarbons Using Di-t-Butyl Peroxide

In a 300-cc autoclave an amount of 56 g of di-t-butyl peroxide was added. Under a $N_2$ pressure, 50 mL of liquid n-butane and 50 mL of liquid propane (to simulate composition for liquefied petroleum gas, LPG) were charged. The autoclave was then heated to 150° C. for 4 h at a stirring rate of 800 rpm. The heat was turned off and the autoclave allowed cooling down to room temperature. A sample was taken and analyzed by GC, indicating complete conversion of di-t-butyl peroxide. A typical GC trace for the LPG coupling products is shown in FIG. 4.

The invention claimed is:

1. A process for the conversion of a feed comprising paraffins to fuel which comprises:
   1. separating the feed into a first fraction comprising isoparaffins and a second fraction consisting of paraffins;
   2. oxidizing the first fraction comprising isoparaffins with air or oxygen to form alkyl hydroperoxides;
   3. converting the alkyl hydroperoxides to dialkyl peroxides;
   4. coupling paraffins in the second fraction using the dialkyl peroxides as radical initiators to form hydrocarbon products of higher molecular weight;
   5. separate the hydrocarbon products of higher molecular weight to obtain a product comprising fuel boiling range hydrocarbons; and
   6. hydrofinishing the product comprising fuel boiling range hydrocarbons to remove trace oxygenates or unsaturation.

2. A process according to claim 1, where the paraffins in step 4 are isoparaffins, normal-paraffins, neoparaffins, cyclic paraffins, or mixtures thereof with carbon numbers in the range of 2 to 12 with the same or different carbon numbers as the isoparaffins of step 2.

3. A process according to claim 1 where the feed is light virgin naphtha.

4. A process according to claim 1 where the feed is liquefied petroleum gas (LPG).

5. A process according to claim 1 where the feed is a mixture of propane, butanes and pentanes.

6. A process according to claim 1 in which the paraffins comprise butanes.

7. A process according to claim 6 in which the feed comprises a mixture of n-butane and iso-butane comprising 5 to 90 wt % iso-butane.

8. A process according to claim 6 in which the feed is n-butane which is isomerized to form iso-butane.

9. A process according to claim 1 in which the paraffins comprise pentanes.

10. A process according to claim 9 in which the feed comprises a mixture of n-pentane, iso-pentane, cyclo-pentane, or neo-pentane.

11. A process according to claim 10 in which the feed is n-pentane.

12. A process according to claim 1 which includes the step of fractionating the hydrocarbon products from step (4) to separate the hydrocarbon products of higher molecular weight.

13. A process according to claim 1 in which the isoparaffins are oxidized to a mixture of alkyl hydroperoxides and alkanols.

14. A process according to claim 1 in which the alkyl hydroperoxides are converted to dialkyl peroxides by reaction of the alkyl hydroperoxides with alkanol.

15. A process according to claim 14 in which the alkyl hydroperoxides are converted to dialkyl peroxides by reaction of the alkyl hydroperoxides with $C_4$ or $C_5$ alkanol.

16. A process according to claim 1 in which the hydrocarbon products of higher molecular weight formed by the coupling of the feed consisting of $C_3$, $C_4$ or $C_5$ paraffins with the dialkyl peroxide are fractionated to separate lower $C_4$ or $C_5$ alkanol and the separated alkanol is partially or fully recycled to step 3 for the formation of dialkyl peroxides.

17. A process according to claim 1 in which the hydrofinishing is performed at a temperature in the range of 150-350° C. and a hydrogen pressure of 1400-7000 KPag (200-1000 psig).

18. A process according to claim 17 in which the hydrofinishing is performed with a catalyst comprising a metal or an alloy on a support.

19. A process according to claim 18 in which the metal or alloy comprises Pt, Pd, Rh, Ru, Ir, Co, Ni, Fe, Cu, Mo, W, Re, or Sn.

20. A process according to claim 18 in which the support comprises alumina, silica, zirconia, titania, carbon, aluminosilicates, zeolites (natural or synthetic), or silicoaluminophosphates (SAPO).

21. A process according to claim 1 in which the hydrocarbon products of higher molecular weight formed by the coupling of the feed consisting of $C_4$ or $C_5$ paraffins with the dialkyl peroxide are fractionated to separate lower $C_4$ or $C_5$ alkanol and the alkanol is dehydrated to form iso-olefins.

22. A process according to claim 1 in which the hydrocarbon products of higher molecular weight formed by the coupling of the feed consisting of $C_4$ or $C_5$ paraffins with the dialkyl peroxide are fractionated to separate lower $C_4$ or $C_5$ alkanol and the alkanol is converted into ether by reacting with an alcohol.

23. A process according to claim 21 where the iso-olefins are converted by oligomerization to higher molecular weight products gasoline, kero-jet, diesel, or lubricant basestocks.

24. A process according to claim 21 where the iso-olefins are converted by alkylation to higher molecular weight products gasoline, kero-jet, or diesel.

25. A process according to claim 1 in which the oxidation of step 2 is carried out at a temperature of 110-150° C. and a pressure of 2000-5500 kPag.

26. A process according to claim 1 in which the oxidation of step 2 is carried out at a temperature of 130-140° C. and a pressure of 2000-3500 kPag.

27. A process according to claim 1 in which the conversion of alkyl hydroperoxides to dialkyl peroxides in step 3 is carried out by reactive distillation.

28. A process according to claim 1 in which the coupling reaction of step 4 is carried out at a temperature of 100-170° C. at a pressure of 3,500-10,000 kPag.

* * * * *